United States Patent [19]

June

[11] Patent Number: 5,429,824
[45] Date of Patent: Jul. 4, 1995

[54] USE OF TYLOXAPOLE AS A NANOPARTICLE STABILIZER AND DISPERSANT

[75] Inventor: Siegfried K. June, Madison, Conn.

[73] Assignee: Eastman Kodak Company, Rochester, N.Y.

[21] Appl. No.: 990,874

[22] Filed: Dec. 15, 1992

[51] Int. Cl.$^6$ ............................. A61K 9/14; A61K 9/51
[52] U.S. Cl. ........................................ 424/489; 424/9.1; 424/490; 424/497; 514/951; 514/975
[58] Field of Search ............... 424/489, 490, 497, 491, 424/492, 494, 496, 498

[56] References Cited

U.S. PATENT DOCUMENTS

| | | | |
|---|---|---|---|
| 4,615,879 | 10/1986 | Runge et al. | 424/9 |
| 5,234,953 | 8/1993 | Crow et al. | 514/573 |
| 5,298,262 | 3/1994 | Na et al. | 424/489 |
| 5,302,401 | 4/1994 | Liversidge et al. | 424/489 |
| 5,318,767 | 6/1994 | Liversidge et al. | 424/4 |
| 5,336,507 | 8/1994 | Na et al. | 424/489 |

FOREIGN PATENT DOCUMENTS 498482  8/1992  United Kingdom .
499299  8/1992  United Kingdom .

Primary Examiner—Thurman K. Page
Assistant Examiner—James M. Spear
Attorney, Agent, or Firm—Arthur H. Rosenstein

[57] ABSTRACT

The present invention is directed to a composition comprised of nanoparticles having tyloxapol adsorbed on the surface thereof. In a preferred embodiment, said nanoparticle contains a diagnostic or therapeutic agent therein. In a further preferred embodiment, the nanoparticles contain a further surface modifier associated therewith. This invention further discloses a method of making nanoparticles having tyloxapol adsorbed on the surface, said method comprising contacting said nanoparticles with tyloxapol for a time and under conditions sufficient to provide a nanoparticle-tyloxapol composition. The present invention is also directed to a method of diagnosis comprising administering to a mammal a contrast effective amount of particles of nanoparticles having tyloxapol adsorbed on the surface thereof, and generating a diagnostic image of said mammal.

10 Claims, No Drawings

USE OF TYLOXAPOLE AS A NANOPARTICLE STABILIZER AND DISPERSANT

FIELD OF THE INVENTION

The present invention is directed to nanoparticles containing a diagnostic or therapeutic agent and tyloxapol associated therewith.

BACKGROUND OF THE INVENTION

Nanoparticles, described in U.S. Pat. No. 5,145,684, are particles consisting of a poorly soluble therapeutic or diagnostic agent onto which are adsorbed a non-crosslinked surface modifier, and which have an average particle size of less than about 400 nanometers (nm).

Tyloxapol (4-(1,1,3,3-tetramethylbutyl)-phenol polymer with ethylene oxide and formaldehyde) is a nonionic liquid polymer of the alkyl aryl polyether alcohol type. Tyloxapol, also known as "Superinone", ms disclosed as useful as a nonionic surface active agent in a lung surfactant composition in U.S. Pat. No. 4,826,821 and as a stabilizing agent for 2-dimethylaminoethyl 4-n-butylaminobenzoate in U.S. Pat. No. 3,272,700.

The present invention is directed to the use of tyloxapol in nanoparticle formulations. Tyloxapol may act as a stabilizer and/or a dispersant. Tyloxapol also functions as a surface modifier. Tyloxapol serves as an excellent wetting agent and affords enhanced blood pool residence via reduced macrophage uptake.

SUMMARY OF THE INVENTION

The present invention is directed to a composition comprised of nanoparticles having tyloxapol adsorbed on the surface thereof. In a preferred embodiment, the nanoparticles are comprised of a diagnostic or therapeutic agent. In a further preferred embodiment, the nanoparticles comprise a further auxiliary surface modifier associated therewith which can function to reduce particle agglomeration during sterilization.

This invention further discloses a method of making nanoparticles having tyloxapol adsorbed on the surface thereof, said method comprising contacting said nanoparticles, comprising an insoluble diagnostic or therapeutic substance, with tyloxapol for a time and under conditions sufficient to provide a corresponding nanoparticle-tyloxapol composition.

The present invention is also directed to a method of diagnosis comprising administering to a mammal a contrast effective amount of particles of nanoparticles having tyloxapol adsorbed on the surface thereof, and generating a diagnostic image of said mammal.

The present invention is further directed to a method of treatment comprising administering to a mammal a therapeutically effective amount of nanoparticles comprising a therapeutic agent having tyloxapol adsorbed on the surface thereof.

DETAILED DESCRIPTION OF THE INVENTION

This invention is described hereinafter primarily in conjunction with tyloxapol as a surface modifier for nanoparticles. However, it is believed that the invention can be practiced with other nonionic liquid polymers of the alkyl aryl polyether alcohol type.

The present invention is directed to a composition comprised of nanoparticles having tyloxapol adsorbed on the surface thereof.

In a preferred embodiment, the nanoparticles comprise a further surface modifier associated therewith. Surface modifiers useful herein physically adhere to the surface of the nanoparticle but do not chemically react with the nanoparticle or itself. Individually adsorbed molecules of the surface modifier are essentially free of intermolecular crosslinkages. Suitable surface modifiers can be selected from known organic and inorganic pharmaceutical excipients such as various polymers, low-molecular weight oligomers, natural products and surfactants. Preferred surface modifiers include nonionic and anionic surfactants.

Representative examples of surface modifiers include gelatin, casein, lecithin (phosphatides), gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens TM, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethylcellulose phthalate, noncrystalline cellulose, magnesium aluminum silicate, triethanolamine, polyvinyl alcohol, and polyvinylpyrrolidone (PVP). Most of these surface modifiers are known pharmaceutical excipients and are described in detail in the *Handbook of Pharmaceutical Excipients*, published jointly by the American Pharmaceutical Association and The Pharmaceutical Society of Great Britain, the Pharmaceutical Press, 1986.

Particularly preferred surface modifiers include polyvinylpyrrolidone, poloxamers such as Pluronic TM F68 and F108, which are block copolymers of ethylene oxide and propylene oxide, and poloxamines such as Tetronic TM 908 (also known as Poloxamine 908), which is a tetrafunctional block copolymer derived from sequential addition of propylene oxide and ethylene oxide to ethylenediamine, available from BASF, dextran, lecithin, dialkylesters of sodium sulfosuccinic acid, such as Aerosol OT TM, which is a dioctyl ester of sodium sulfosuccinic acid, available from American Cyanamid, Duponol TM P, which is a sodium lauryl sulfate, available from DuPont, Triton TM X-200, which is an alkyl aryl polyether sulfonate, available from Rohm and Haas, Tween 80, which is a polyoxyethylene sorbitan fatty acid ester, available from ICI Specialty Chemicals, and Carbowax TM 3350 and 934, which are polyethylene glycols available from Union Carbide. Surface modifiers which have been found to be particularly useful include Tetronic 908, the Tweens TM, Pluronic F-68 and polyvinylpyrrolidone. Other useful surface modifiers include:

decanoyl-N-methylglucamide;
n-decyl β-D-glucopyranoside;
n-decyl β-D-maltopyranoside;
n-dodecyl β-D-glucopyranoside;
n-dodecyl β-D-maltoside;
heptanoyl-N-methylglucamide
n-heptyl β-D-glucopyranoside;
n-heptyl β-D-thioglucoside;
n-hexyl β-D-glucopyranoside;
nonanoyl-N-methylglucamide;
n-nonyl β-D-glucopyranoside;

octanoyl-N-methylglucamide;

n-octyl β-D-glucopyranoside;

octyl β-D-thioglucopyranoside; and the like.

Particularly preferred auxiliary surface modifiers are those which impart resistance to particle aggregation during sterilization and include dioctylsulfosuccinate (DOSS), polyethylene glycol, glycerol, sodium dodecyl sulfate, dodecyl trimethyl ammonium bromide and a charged phospholipid such as dimyristoyl phophatidyl glycerol. The surface modifiers are commercially available and/or can be prepared by techniques known in the art. Two or more surface modifiers can be used in combination.

The tyloxapol that is associated with the nanoparticles may function as a surface modifier, as a stabilizer, and/or as a dispersant. Alternatively, the tyloxapol may serve other purposes. In one embodiment of the present invention, tyloxapol serves all three functions. In another embodiment, the tyloxapol may serve as a stabilizer and/or a dispersant, whereas another compound acts as a surface modifier, as discussed elsewhere herein.

The nanoparticles of the present invention contain a diagnostic or therapeutic agent. The nanoparticles useful in the practice of this invention can be prepared according to the methods disclosed in U.S. Pat. No. 5,145,684, whose disclosure is incorporated herein by reference. Briefly, nanoparticles are prepared by dispersing a poorly soluble therapeutic or diagnostic agent in a liquid dispersion medium and wet-grinding the agent in the presence of grinding media to reduce the particle size of the contrast agent to an effective average particle size of less than about 400 nm. The particles can be reduced in size in the presence of a surface modifier.

A general procedure for preparing the particles useful in the practice of this invention follows. The therapeutic or diagnostic agent selected is obtained commercially and/or prepared by techniques known in the art as described above, in a conventional coarse form. It is preferred, but not essential, that the particle size of the coarse therapeutic or diagnostic substance selected be less than about 100 $\mu$m as determined by sieve analysis. If the coarse particle size of that agent is greater than about 100 $\mu$m, then it is preferred that the coarse particles of the therapeutic or diagnostic agent be reduced in size to less than 100 $\mu$m using a conventional milling method such as airjet or fragmentation milling.

The coarse therapeutic or diagnostic agent selected can then be added to a liquid medium in which it is essentially insoluble to form a premix. The concentration of the therapeutic or diagnostic agent in the liquid medium can vary from about 0.1–60%, and preferably is from 5–30% (w/w). It is preferred, but not essential, that the surface modifier be present in the premix. The concentration of the surface modifier can vary from about 0 1 to 90% and preferably is 1–75%, more preferably 10–60% and most preferably 10–30% by weight based on the total combined weight of the drug substance and surface modifier. The apparent viscosity of the premix suspension is preferably less than about 1000 centipoise.

The premix can be used directly by wet grinding to reduce the average particle size in the dispersion to less than 400 nm. It is preferred that the premix be used directly when a ball mill is used for attrition. Alternatively, the therapeutic or diagnostic agent and, optionally, the surface modifier, can be dispersed in the liquid medium using suitable agitation, e.g., a roller mill or a Cowles type mixer, until a homogeneous dispersion is observed in which there are no large agglomerates visible to the naked eye. It is preferred that the premix be subjected to such a premilling dispersion step when a recirculating media mill is used for attrition.

Wet grinding can take place in any suitable dispersion mill, including, for example, a ball mill, an attritor mill, a vibratory mill, and media mills such as a sand mill and a bead mill. A media mill is preferred due to the relatively shorter milling time required to provide the intended result, i.e., the desired reduction in particle size. For media milling, the apparent viscosity of the premix preferably is from about 100 to about 1000 centipoise. For ball milling, the apparent viscosity of the premix preferably is from about 1 up to about 100 centipoise. Such ranges tend to afford an optimal balance between efficient particle fragmentation and media erosion.

The grinding media for the particle size reduction step can be selected from rigid media preferably spherical or particulate in form having an average size less than about 3 mm and, more preferably, less than about 1 mm. Such media desirably can provide the particles of the invention with shorter processing times and impart less wear to the milling equipment. The selection of material for the grinding media is not believed to be critical. However, preferred media have a density greater than about 3 g/cm$^3$. Zirconium oxide, such as 95% ZrO stabilized with magnesia, zirconium silicate, and glass grinding media provide particles having levels of contamination which are believed to be acceptable for the preparation of therapeutic or diagnostic compositions. However, other media, such as stainless steel, titania, alumina, and 95% ZrO stabilized with yttrium, are believed to be useful.

The attrition time can vary widely and depends primarily upon the particular wet grinding mill selected. For ball mills, processing times of up to five days or longer may be required. On the other hand, processing times of less than 1 day (residence times of about one minute up to several hours) have provided the desired results using a high shear media mill.

The particles must be reduced in size at a temperature which does not significantly degrade the therapeutic or diagnostic agent. Processing temperatures of less than about 30°–40° C. are ordinarily preferred. If desired, the processing equipment can be cooled with conventional cooling equipment. The method is conveniently carried out under conditions of ambient temperature and at processing pressures which are safe and effective for the milling process. For example, ambient processing pressures are typical of ball mills, attritor mills and vibratory mills. Processing pressures up to about 20 psi (1.4 kg/cm$^2$) are typical of media milling.

The surface modifier, if not present in the premix, must be added to the dispersion after attrition in an amount as described for the premix. Thereafter, the dispersion can be mixed, e.g., by shaking vigorously. Optionally, the dispersion can be subjected to a sonication step, e.g., using an ultrasonic power supply. For example, the dispersion can be subjected to ultrasonic energy having a frequency of 20–80 kHz for a time of about 1 to 120 seconds.

The relative amount of therapeutic or diagnostic agent and surface modifier can vary widely and the optimal amount of the surface modifier can depend, for example, upon the particular therapeutic or diagnostic agent and surface modifier selected, the critical micelle concentration of the surface modifier if it forms micelles, the hydrophilic lipophilic balance (HLB) of the stabilizer, the melting point of the stabilizer, its water solubility, the surface tension of water solutions of the stabilizer, etc. The surface modifier preferably is present in an amount of about 0.1–10 mg per square meter surface area of the therapeutic or diagnostic agent. The surface modifier can be present in an amount of 0.1–90%, preferably 1–75%, more preferably 10–60%, and most preferably 10–30% by weight based on the total weight of the dry particle.

Therapeutic and diagnostic agents useful in the composition of the present invention include those disclosed in U.S. Pat. No. 5,145,684, and EP-A 498,482, whose disclosures are hereby incorporated by reference. Preferred diagnostic agents include ethyl 3,5-diacetoamido-2,4,6-triiodobenzoate (WIN 8883), ethyl-2- (3,5-bis (acetamido)-2,4,6-triiodobenzoyloxy)butyrate (WIN 16318), diethyl 2-(3,5-bis (acetamido) -2,4,6-triiodobenzoyloxy malonate (WIN 67721), and 6-ethoxy-6-oxohexyl-3,5-bis (acetamido) -2,4,6-triiodobenzoate (WIN 67722). A particularly preferred diagnostic agent is the x-ray imaging agent WIN 8883.

As used herein, particle size refers to a number average particle size as measured by conventional particle size measuring techniques well known to those skilled in the art, such as sedimentation field flow fractionation, photon correlation spectroscopy, or disk centrifugation. By "an effective average particle size of less than about 400 nm" it is meant that at least 90% of the particles have a weight average particle size of less than about 400 nm when measured by the above-noted techniques. In preferred embodiments of the invention, the effective average particle size is less than about 300 nm, and more preferably less than about 250 nm. In some embodiments of the invention, an effective average particle size of less than about 200 nm has been achieved. With reference to the effective average particle size, it is preferred that at least 95% and, more preferably, at least 99% of the particles have a particle size less than the effective average, e.g., 400 nm. In particularly preferred embodiments, essentially all of the particles have a size less than 400 nm. In some embodiments, essentially all of the particles have a size less than 250 nm.

The present invention includes the nanoparticle composition with tyloxapol associated on the surface thereof, as described elsewhere herein, formulated into compositions together with one or more non-toxic physiologically acceptable carriers, adjuvants or vehicles which are collectively referred to herein as carriers, for parenteral injection, for oral administration in solid or liquid form, for rectal or topical administration, or the like.

The compositions can be administered to humans and animals either orally, rectally, parenterally (intravenous, intramuscular or subcutaneous), intracisternally, intravaginally, intraperitoneally, locally (powders, ointments or drops), or as a buccal or nasal spray.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Solid dosage forms for oral administration include capsules, tablets, pills, powders and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays and inhalants. The active component is admixed under sterile conditions with a physiologically acceptable carrier and any preservatives, buffers or propellants as may be required. Ophthalmic formulations, eye ointments, powders and solutions are also contemplated as being within the scope of this invention.

Actual dosage levels of active ingredients in the compositions of the present invention may be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors.

The total daily dose of the compounds of this invention administered to a host in single of divided dose may be in amounts, for example, of from about 1 nanomol to about 5 micromoles per kilogram of body weight. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

A method for the preparation of a nanoparticle composition according to this invention includes the steps of introducing a therapeutic or diagnostic agent, a liquid medium, grinding media, and optionally, a surface modifier into a grinding vessel; wet grinding to reduce the particle size of the therapeutic or diagnostic agent to less than about 400 nm; and separating the particles and optionally the liquid medium from the grinding vessel and grinding media, for example, by suction, filtration or evaporation. If the surface modifier is not present during wet grinding it can be admixed with the particles thereafter. The liquid medium, most often water, can serve as the pharmaceutically acceptable carrier. The method preferably is carried out under aseptic conditions. Thereafter, the nanoparticle composition preferably is subjected to a sterilization process.

This invention further discloses a method of making nanoparticles having tyloxapol adsorbed on the surface thereof, said method comprising contacting said nanoparticles with tyloxapol for a time and under conditions sufficient to provide a nanoparticle-tyloxapol composition.

This method involves the preparation of therapeutic or diagnostic nanoparticles, as discussed elsewhere herein, and contacting those nanoparticles with tyloxapol. Contacting may be by admixing a suspension of nanoparticles with a solution of tyloxapol for a time period and under conditions suitable for the formation of a nanoparticle-tyloxapol composition.

The concentration of tyloxapol can vary from about 0.1 to 90% and preferably is 1–75% more preferably 10–60% and most preferably 10–30% by weight based on the total combined weight of the drug substance and tyloxapol. The time of contacting may be from 60 seconds to about 48 hours.

In a preferred embodiment, the method comprises the further addition of other surface modifiers associated with the nanoparticles. The method is practiced according to the techniques described elsewhere herein.

The present invention is also directed to a method of diagnosis comprising administering to a mammal a contrast effective amount of particles of nanoparticles having tyloxapol adsorbed on the surface thereof, and generating a diagnostic image of said mammal. In a preferred embodiment, the nanoparticles comprise a further surface modifier associated therewith.

A method for diagnostic imaging for use in medical procedures in accordance with this invention comprises administering to the body of a test subject in need of a diagnostic image an effective contrast producing amount of the above-described diagnostic image contrast composition. In addition to human patients, the test subject can include mammalian species such as rabbits, dogs, cats, monkeys, sheep, pigs, horses, bovine animals and the like. Thereafter, at least a portion of the body containing the administered contrast agent is exposed to x-rays or a magnetic field to produce an x-ray or magnetic resonance image pattern corresponding to the presence of the contrast agent. The image pattern can then be visualized.

In x-ray imaging, transmitted radiation is used to produce a radiograph based upon overall tissue attenuation characteristics. X-rays pass through various tissues and are attenuated by scattering, i.e., reflection or refraction or energy absorption. However, certain body organs, vessels and anatomical sites exhibit so little absorption of x-ray radiation that radiographs of these body portions are difficult to obtain. To overcome this problem, radiologists routinely introduce an x-ray absorbing medium containing a contrast agent into such body organs, vessels and anatomical sites.

Any x-ray visualization technique, preferably, a high contrast technique such as computed tomography, can be applied in a conventional manner. Alternatively, the image pattern can be observed directly on an x-ray sensitive phosphor screen-silver halide photographic film combination.

Visualization with a magnetic resonance imaging system can be accomplished with commercially available magnetic imaging systems such as a General Electric 1.5 T Sigma imaging system [1H resonant frequency 63.9 megahertz (MHz)]. Commercially available magnetic resonance imaging systems are typically characterized by the magnetic field strength used, with a field strength of 2.0 Tesla as the current maximum and 0.2 Tesla as the current minimum. For a given field strength, each detected nucleus has a characteristic frequency. For example, at a field strength of 1.0 Tesla, the resonance frequency for hydrogen is 42.57 MHz; for phosphorus-31 it is 17.24 MHz; and for sodium-23 it is 11.26 MHz.

A contrast effective amount of the compositions of the present invention is that amount necessary to provide tissue visualization with, for example, magnetic resonance imaging or x-ray imaging. Means for determining a contrast effective amount in a particular subject will depend, as is well known in the art, on the nature of the magnetically reactive material used, the mass of the subject being imaged, the sensitivity of the magnetic resonance or x-ray imaging system and the like.

After administration of the compositions of the present invention, the subject mammal is maintained for a time period sufficient for the administered compositions to be distributed throughout the subject and enter the tissues of the mammal. Typically, a sufficient time period is from about 20 minutes to about 90 minutes and, preferably from about 20 minutes to about 60 minutes.

The following examples further illustrate the invention and are not to be construed as limiting of the specification and claims in any way. Specific embodiments of the invention are illustrated in the following examples:

EXAMPLE 1

Imaging studies with Tyloxapol and ethyl 3,5-diacetoamido-2,4,6-triiodobenzoate (WIN 8883)

A formulation of WIN 8883 was prepared using Tyloxapol as the stabilizer in the amounts of 20 grams (gm) of WIN 8883 per 100 ml of suspension and 3 gm of tyloxapol per 100 ml of suspension in phosphate buffered saline (PBS). The suspension was milled for 7 days after which the average particle size was determined by light scattering to be 185 nm. Stability testing in fresh rat plasma and simulated gastric fluid did not show any aggregation. The formulation was sent for computer-aided tomography X-ray imaging studies at both the Center for Imaging and Pharmaceutical Research (CIPR) at the Massachusetts General Hospital and at Stanford University Medical School, Department of Radiology.

At CIPR, the Tyloxapol suspension provided excellent images of axillary and subscapular lymph nodes upon injection in the forepaws of male, white New Zealand rabbits (approximate weight=2.5 k g) at times of 12 and 36 hours post injection of 0.5 ml as a single bolus injection. At Stanford, the injection of 3 ml/kg afforded excellent imaging of the vasculature followed by opacification of both the liver and spleen at long times post injection (i.e., >30 min.).

EXAMPLE 2

Imaging studies with Tyloxapol and WIN 16318

A formulation of WIN 16318 was prepared as in Example 1 only using 10 gm of WIN 16318 per 100 ml formulation and 3.4 gm of Tyloxapol per 100 ml of formulation and milling for 14 days. At the end of this process, the particle size was determined by light scattering to be 289 nm. The formulation was sent to Stanford for imaging studies where IV injection resulted in prolonged blood pool opacification followed by concentration within the liver and spleen.

EXAMPLE 3.

Imaging Studies with Tyloxapol and WIN 8883

A formulation was prepared as in Example 1 using 10 gm of WIN 8883 per 100 ml formulation and 3 gm of Tyloxapol per 100 ml formulation. After milling for 7 days, the particle size was determined to be 170 nm by light scattering. Imaging at CIPR demonstrated excellent imaging of axillary and subscapular lymph nodes at 12 hours post injection.

EXAMPLE 4

Imaging Studies with Tyloxapol and WIN 67721

A formulation was prepared as in Example 1 only using 15 gm of WIN 67721 per 100 formulation and 4.0 gm of Tyloxapol per 100 ml of formulation. After milling for 3 days, the particle size was determined to be 207 nm by light scattering. Imaging at CIPR demonstrated excellent axillary and subscapular lymph node opacification after injection of 0.5 ml subcutaneously in the forepaw of the rabbits at 12 hours post injection.

EXAMPLE 5

Imaging Studies with Tyloxapol and WIN 67722

A formulation was prepared as in Example 4 only using WIN 67722. The suspension was milled for 3 days and achieved a particle size of 186 nm as determined by light scattering. Imaging at CIPR demonstrated excellent axillary and subscapular lymph node opacification after injection of 0.5 ml subcutaneously in the forepaw of the rabbit at times of 12 hr post injection.

EXAMPLE 6

During extensive screening studies involving over 40 poorly soluble compounds, it was found that tyloxapol stabilized a much higher percentage (about 80%) of compounds in the form of nanoparticles than all other surface modifiers tested.

EXAMPLE 7

Tyloxapol Stabilized Retinoic Acid Nanoparticles

Tyloxapol was shown to be a good stabilizer for the therapeutic compound retinoic acid. A nanoparticle formulation (7% retinoic acid, 3% tyloxapol) wet-milled according to the technique described in U.S. Pat. No. 5,145,684 to a mean particle size of 130 nm exhibited a mean particle size of 145 nm seven months later.

The foregoing specification, including the specific embodiments and examples is intended to be illustrative of the present invention and is not to be taken as limiting. Numerous other variations and modifications can be effected without departing from the true spirit and scope of the present invention.

I claim:

1. A composition comprised of nanoparticles consisting essentially of 99.9–10% by weight of an organic crystalline therapeutic or diagnostic agent having tyloxapol adsorbed on the surface thereof in an amount of 0.1–90% by weight and sufficient to maintain an average particle size of less than 400 nm.

2. A composition comprised of nanoparticles consisting essentially of 99.9–10% by weight of an organic crystalline therapeutic or diagnostic agent having tyloxapol adsorbed on the surface thereof in an amount of 0.1–90% by weight and sufficient to maintain an average particle size of less than 400 nm. and an additional surface modifier associated therewith.

3. The composition of claim 1 wherein said nanoparticles contain a diagnostic agent therein.

4. A composition comprised of nanoparticles containing a diagnostic agent having tyloxapol adsorbed on the surface thereof, wherein said diagnostic agent is ethyl 3,5-diacetoamido-2,4,6-triiodobenzoate.

5. A method of making nanoparticles consisting essentially of 99.9–10% by weight an organic crystalline therapeutic or diagnostic agent having tyloxapol adsorbed on the surface thereof in an amount of 0.1–90% by weight and sufficient to maintain an average particle size of less than 400 nm, said method comprising contacting said therapeutic or diagnostic agent with tyloxapol for a time and under conditions sufficient to provide a nanoparticle-tyloxapol composition.

6. A method of making nanoparticles consisting essentially of 99.9–10% by weight of an organic crystalline therapeutic or diagnostic agent having tyloxapol adsorbed on the surface thereof in an amount of 0.1–90% by weight and sufficient to maintain an average particle size of less than 400 nm., and an additional surface modifier associated therewith, said method comprising contacting said therapeutic or diagnostic agent with tyloxapol for a time and under conditions sufficient to provide a nanoparticle-tyloxapol composition.

7. The method of claim 5 wherein said nanoparticles contain a diagnostic agent therein.

8. A method of making nanoparticles containing a diagnostic agent having tyloxapol adsorbed on the surface thereof, said method comprising contacting said diagnostic agent with tyloxapol for a time and under conditions sufficient to provide nanoparticle-tyloxapol composition, wherein said diagnostic agent is ethyl 3,5-diacetoamido-2,4,6-triiodobenzoate.

9. A composition comprised of nanoparticles containing a diagnostic agent having tyloxapol adsorbed on the surface thereof, wherein said diagnostic agent is selected from the group consisting of:
ethyl 3,5-diacetoamido-2,4,6-triiodobenzoate,
ethyl-2-(3,5-bis (acetamido) -2,4,6-triiodobenzoyloxy)butyrate,
diethyl 2-(3,5-bis (acetamido) -2,4,6-triiodobenzoyloxy)malonate and
6-ethoxy-6-oxohexyl-3,5-bis (acetamido) -2,4,6-triiodobenzoate.

10. A method of making nanoparticles containing a diagnostic agent having tyloxapol adsorbed on the surface thereof, said method comprising contacting said nanoparticles with tyloxapol for a time and under conditions sufficient to provide a nanoparticle-tyloxapol composition, wherein said diagnostic agent is selected from the group consisting of:
ethyl 3,5-diacetoamido-2,4,6-triiodobenzoate,
ethyl-2-(3,5-bis (acetamido)-2,4,6-triiodobenzoyloxy)butyrate,
diethyl 2-(3,5-bis (acetamido)-2,4,6-triiodobenzoyloxy)malonate and
6-ethoxy-6-oxohexyl-3,5-bis (acetamido)-2,4,6-triiodobenzoate.

* * * * *